United States Patent [19]
Albrecht et al.

[11] Patent Number: 5,491,125
[45] Date of Patent: Feb. 13, 1996

[54] LIQUID HERBICIDAL FORMULATIONS OF GLUFOSINATE

[75] Inventors: Konrad Albrecht, Kelkheim; Jean Kocur; Peter Langelüddeke, both of Hofheim am Taunus, all of Germany

[73] Assignee: Hoechst Aktiengesellschaft, Germany

[21] Appl. No.: 983,964

[22] Filed: Dec. 1, 1992

Related U.S. Application Data

[63] Continuation of Ser. No. 884,266, May 8, 1992, abandoned, which is a continuation-in-part of Ser. No. 324,405, Mar. 16, 1989, abandoned.

[30] Foreign Application Priority Data

Mar. 18, 1988 [DE] Germany ............ 38 09 159.3

[51] Int. Cl.[6] .................. A01N 57/12; A01N 57/20
[52] U.S. Cl. ...................... 504/206; 504/116
[58] Field of Search .................. 504/206

[56] References Cited

U.S. PATENT DOCUMENTS

| | | | |
|---|---|---|---|
| 4,048,039 | 9/1977 | Daxinger | 204/192.28 |
| 4,101,200 | 7/1978 | Daxinger | 359/585 |
| 4,120,688 | 10/1978 | Otten | 504/201 |
| 4,159,901 | 7/1979 | Beestman | 504/206 |
| 4,168,963 | 9/1979 | Rupp | 504/201 |
| 4,400,196 | 8/1983 | Albrecht | 504/206 |
| 4,439,344 | 3/1984 | Albanese | 71/DIG. 1 |
| 5,152,823 | 10/1992 | Albrecht et al. | 504/130 |
| 5,258,358 | 11/1993 | Kocur et al. | 504/205 |

FOREIGN PATENT DOCUMENTS

| | | |
|---|---|---|
| 1162071 | 2/1984 | Canada . |
| 0048436 | 3/1982 | European Pat. Off. . |
| 1542926 | 4/1970 | Germany . |
| 2554232 | 9/1976 | Germany . |
| 2725823 | 12/1978 | Germany . |
| 3008186A1 | 10/1981 | Germany . |
| 2178960 | 2/1987 | United Kingdom . |

OTHER PUBLICATIONS

Chemical Patents Index, Basic Abstracts Journal, Section C, AGDOC (Apr. 1, 1987).
Otsuka Kagaku Yakuhin, *Central Patents Index, Basic Abstracts Journal*, (1978).

Primary Examiner—S. Mark Clardy
Assistant Examiner—B. Bembenick
Attorney, Agent, or Firm—Curtis, Morris & Safford

[57] ABSTRACT

Liquid herbicidal agents which contain a compound of the formula

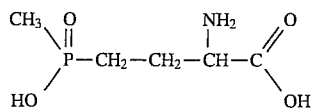

in the form of the racemate or of the L enantiomer, lower alkyl esters thereof or salts thereof with acids or bases (I) in combination with surfactants in the form of a) alkyldimethyl-, fatty acid amidopropyldimethyl- or fatty acid amido ethyldimethylamine oxides or b) the betaine of coconut alkyldimethylaminoacetic acid or of coconut alkylaminopropionic acid or c) alkanesulfonates and mixtures thereof with fatty alcohol polyglycol ether sulfosuccinic acid monoesters or fatty alcohol polyglycol ether sulfates or d) alkylsulfosuccinic acid monoesters or fatty alcohol polyglycol ether sulfosuccinic acid monoesters and fatty alcohol polyglycol ether sulfosuccinic esters and their mixtures with fatty alcohol polyglycol ether sulfates or e) α-olefinsulfonates and mixtures thereof with fatty alcohol polyglycol ether sulfates, fatty alcohol polyglycol ether sulfosuccinic acid monoesters or alkylsulfosuccinic acid monoesters, sulfonates which can be used being alkali metal salts, ammonium salts, alkaline earth metal salts or substituted alkyl- or alkanolamine salts of the corresponding sulfonic or sulfuric acids, which possess improved herbicidal activities, high low-temperature stability and rain resistance and are distinguished by a low content of organic solvents.

5 Claims, No Drawings

LIQUID HERBICIDAL FORMULATIONS OF GLUFOSINATE

This application is a continuation of application Ser. No. 07/884,266, filed May 8, 1992, (abandoned) which in turn was a continuation-in part of application Ser. No. 07/324,405, filed Mar. 16, 1989 (abandoned).

U.S. Pat. No. 4,168,963 discloses that compounds of the formula

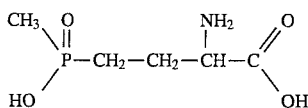

and their derivatives (I) possess a good and broad activity against weeds of many botanical families. The compounds I contain an asymmetric carbon atom. Formula I encompasses all stereoisomers (D and L form), in particular the biologically active L enantiomer. The ammonium salt of these compounds (both L form and racemate) is particularly important.

The compounds are suitable for the non-selective control of undesired plant growth, for example on agricultural cropped areas, in viticulture, in orchards and oil palm plantations, and on industrial terrain and rail tracks. They are usually formulated as aqueous solutions.

Furthermore, it has been disclosed that the activity of herbicides can be improved in many cases by the addition of surface-active agents (cf. German Offenlegungsschriften 2,725,823 and 2,554,232). ($C_{12}$–$C_{18}$)-Fatty alcohol polyglycol ether and alkylphenol polyglycol ether are used particularly frequently for this purpose. EP-A 0,048,436 shows that coconut fat alkylbenzyldimethylammonium chloride or $C_{12}$–$C_{18}$-alkyl polyglycol ether sulfates enhance the action of I compared with the fatty alcohol polyglycol ethers and alkylphenol polyglycol ethers which were included in the comparison test. However, the water-containing liquid formulations of I are only stable when polar solvents, such as, for example, dimethylformamide, N-methylpyrrolidone or ethylene glycol monomethyl ether are added. Otherwise, phase separation occurs in the formulation to give phases which are enriched in active substance and relatively poor in surfactants and phases which are relatively poor in active substances an enriched in surfactants.

Furthermore, it has emerged that low-temperature stability of the formulations is often insufficient for practical requirements. Even though active substance or surfactant only precipitate below freezing point between 0° and −10° C., problems may still occur when preparations which are stored under conditions where they may be exposed to frost are drawn off from larger containers into small casks. Thus, for example, the large casks have to be stored in the warmth for a relative long time so that active substance and surfactant redissolve and the formulation can be drawn off homogeneously into small packages. Moreover, the preparations should contain no, or the smallest possible amounts, of organic solvents due to the flammability and potential hazard for the user. It is also important to improve rain resistance of the formulations which contain compounds of the formula I or derivatives thereof as active substance since these active substances are water-soluble and are taken up by the plants via the leaf surface. Above all in tropical areas, there is thus the danger of the active substance being washed away from the leaf surface due to rain starting after the application and thus becoming inefficient. Additions of adhesives, as they are used in wettable powders for improving rain resistance, for example polyvinyl alcohols, polyvinylpyrrolidones, polyvinyl acrylates, polyvinyl acetates, hydroxyethylcelluloses, carbethoxyethylcelluloses, methylcelluloses, dextrins, hydrolysed peptides, heteropolysaccharides, ligninsulfonates, cation-active compounds or mineral oils were shown to be ineffective in experiments. From the practical point of view, in particular the following requirements have thus to be made for the liquid formulations of compounds of the formula I:

a) high low-temperature stability b) better herbicidal action compared with the known formulations c) good rain resistance and:

d) amount of organic solvents added as small as possible.

Surprisingly, it has been found that formulations of the abovementioned active substances, which exhibit these improved properties, can be obtained by using certain surfactants.

The present invention thus relates to liquid herbicidal agents containing a compound of the formula

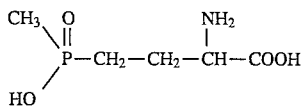

in the form of the racemate or of the L enantiomer, lower alkyl esters thereof or salts thereof with acids or bases (I) in combination with surfactants in the form a) ($C_{12}$–$C_{18}$)-alkyldimethyl-, ($C_{10}$–$C_{18}$)-fatty acid amidopropyldimethyl- or ($C_{10}$–C18)-fatty acid amido ethyldimethylamine oxides or b) the betaine of coconut alkyldimethylaminoacetic acid or of coconut alkylaminopropionic acid or c) ($C_{12}$–$C_{18}$)-alkanesulfonates and mixtures thereof with ($C_{10}$–$C_{18}$)-fatty alcohol polyglycol ether sulfosuccinic acid monoesters or ($C_{10}$–$C_{18}$)-fatty alcohol polyglycol ether sulfates or d) ($C_{12}$–$C_{18}$)-alkylsulfosuccinic acid monoesters or ($C_{10}$–$C_{18}$)-fatty alcohol polyglycol ether sulfosuccinic acid monoesters and ($C_{10}$–$C_{18}$)-fatty alcohol polyglycol ether sulfosuccinic acid esters and their mixtures with ($C_{10}$–$C_{18}$)-fatty alcohol polyglycol ether sulfates or e) ($C_{12}$–$C_{20}$)--olefinsulfonates and mixtures thereof with ($C_{10}$–$C_{18}$)-fatty alcohol polyglycol ether sulfates, ($C_{10}$–$C_{18}$)-fatty alcohol polyglycol ether sulfosuccinic acid monoesters or ($C_{12}$–$C_{18}$)-alkylsulfosuccinic acid monoesters, sulfonates which can be used being alkali metal salts, ammonium salts, alkaline earth metal salts or substituted alkyl- or alkanolamine salts of the corresponding sulfonic or sulfuric acids.

Surfactants which are preferably used are ($C_{12}$–$C_{18}$)-alkyldimethylamine oxides, ($C_{12}$–$C_{18}$)-alkanesulfonates, ($C_{12}$–$C_{18}$)-alkylsulfosuccinic acid monoesters, here in particular isodecylsulfosuccinic acid monoester, and ($C_{12}$–$C_{20}$)-α-olefinsulfonates and the mixtures of these compounds with ($C_{10}$–$C_{18}$)-fatty alcohol polyglycol ether sulfates.

A further preferred embodiment of the agents according to the invention comprises, besides 5–40 % by weight of a compound I, the 0.5–8-fold proportion by weight of the surfactants according to the invention and 0–20% by weight of a water-miscible polar solvent, for example methylglycol, propyleneglycol monomethyl ether, PEG 200, isopropanol, DMF or NMP.

The ready formulation contains further surface-active substances in amounts of in particular between 4–15% by weight.

The agents according to the invention contain 5–40% by weight of an active substance of the formula I in the form of an aqueous solution and 0.5–8 parts of the surfactants according to the invention per part of active substance.

Further surface-active agents for improving the wettability, adhesives and binders, urea or inorganic salts such as for example ammonium sulfate, water-soluble solvents and defoamers may additionally be present. These surfactants can also be advantageously employed in combination formulations of a compound I with other herbicidal active substances, for example simazin, terbutylazin, diuron, monolinuron, metolachlor, chlortoluron, oxyfluorfen, bifenox, imazethapyr, chlorimuron-ethyl, sulfonyl ureas, for example sulfometuron, metsulfuron, and they can enhance the action of I.

Alternatively, the surfactants can be added prior to application directly to the slurry of the active substance solution of I or to the mixed formulations with the herbicides mentioned.

The agents according to the invention are present as solutions, in mixtures with water-insoluble active substances, for example the abovementioned triazine active substances and urea herbicide active substances, as suspension concentrates in which the insoluble active substances are present in the solid phase, and the compound I and the surfactants according to the invention in the aqueous liquid phase. Active substances of low melting point or liquid active substances, such as metolachlor, are prepared with a compound I and the surfactants in the form of a stable emulsion in which the compound I and the surfactants according to the invention are present in the aqueous phase and the water-insoluble liquid or the active substance, dissolved in organic solvents, is present in the "oily" liquid phase, where the organic solvents themselves should not be water-soluble.

Mixed formulations of this type can be prepared in many ways. On the one hand, a procedure can be followed in which individual components are prepared separately in the form of individual dispersions and solutions, and these are then mixed using a colloid mill. Likewise, it is possible to grind the active substances of the finely-disperse phase together and to add the active substance solution to this mixed dispersion. In principle, it is also possible to process all active substances in one run to give the desired mixed formulation.

The combination formulations prepared in this manner are storage-stable, show virtually no chemical changes and are simple to apply for use.

The agents according to the invention are applied following dilution in water. Suitable active substances of the compound I are in particular those compounds which are described in U.S. Pat. No. 4,168,963 or which can be prepared accordingly, for example (3-amino-3-carboxypropyl)-methylphosphinic acid (phosphinothricin), its hydrochloride, monosodium salt, disodium salt, monopotassium salt, dipotassium salt, monocalcium salt, ammonium salt, $NH_3(CH_3)^+$ salt, $NH_2(CH_3)_2$ salt, $NH(CH_3)_3$ salt, $NH(CH_3)_2(C_2H4OH)^+$ or $NH_2(CH_3)(C_2H_4OH)^+$ salt, or its methyl ester, ethyl ester, propyl ester or butyl ester.

To prepare the agents according to the invention, the active substance is dissolved in water, the calculated amount of action-enhancing surface-active agent and if desired further customary auxiliaries, such as solubilizers (propylene glycol monomethyl ether, glycols, polyglycols, block polymers, DMF, N-methylpyrrolidone and the like), other surfactants, colorants or defoamers (for example silicones, polyethylene polypropylene glycols, soaps and the like), are added and the batch is mixed intimately.

The surfactants according to the invention and the other customary formulation auxiliaries are described, for example, in: Watkins, "Handbook of Insecticide Dust Diluents and Carriers", 2nd Ed., Darland Books, Caldwell N. J.; H. v.Olphen, "Introduction to Clay Colloid Chemistry", 2nd Ed., J. Wiley & Sons, New York: Marschen, "Solvents Guide", 2nd Ed., Interscience, New York 1950; McCutcheon's, "Detergents and Emulsifiers Annual", MC Publ. Corp., Ridgewood N.J.; Sisley and Wood, "Encyclopedia of Surface Active Agents", Chem. Publ. Co. Inc. New York 1964; Schönfeldt, "Grenzflächenaktive Äthylenoxidaddukte" [Surface-active ethylene oxide adducts], Wisconsin Verlagsgesell., Stuttgart 1976; Winnacker-Küchler, "Chemische Technologie" [Chemical Technology], Volume 7, C Hauser Verlag München, 4th Edition 1986.

Examples of the surfactants according to the invention which may be mentioned are:

$(C_{12}-C_{18})$-alkyldimethylamine oxides: Alkamox Lo® (Alkaril Chemicals), Aromox DMM CD-N® (Akzo Chemie), Genaminox® (Hoechst AG), Nissan Unisafe ALM (Nippon Oil & Fats Co.)

Fatty acid amidopropyldimethylamine oxides: Alkamox CAPO® (Alkaril Chem.) Rewominox B 204® ((Rewo Chem. Werke), Steinapon AM B13® (Rewo Chem. Werke)

Betaines of, for example, coconut alkyldimethylaminoacetic acid: ALkateric BC® (Alkaril Chemicals), Armorteric IB® (Akz) or coconut alkylaminopropionic acid: Alkateric AP-C® (Alkaril Chemicals), Amphoteric B4® (Zschimmer & Schwarz)

Isodecylsulfosuccinic acid ester: Netzer IS® (Hoechst AG)

Sulfosuccinic acid esters based on fatty alcohol polyglycol ethers are: Texapon SB 3® (Henkel KG), Setacin 103® (Zschimmer & Schwarz), Genopur SB 3120® (Hoechst AG), Elfanol 616® (Akzo Chem.), Konacool-L400® (Toko Chem. Ind. Co. Ltd.)

$C_{12}-C_{18}$)-alkanesulfonate: Hostapur SAS® (Hoechst AG)

α-Olefinsulfonates: Elfanol OS46® (Akzo Chemie), Hostapur OS45® (Hoechst AG)

Fatty alcohol polyglycol ether sulfates: Genapol LRO®, Genapol LRC®, (Hoechst AG), Gezavon LL 20® (Zimmerli AG), Texapon ASV®, Texapon Na®, Texapon M (Henkel KG)

$(C_{12}-C_{18})$-alkylsulfates: Texapon K 12® (Henkel KG)

The following examples serve to illustrate the invention:

TABLE 1

A) Composition and stability of active substance formulations according to the invention

| Formulation No. | Active substance % | Water % | Organic Solvent % | Surface-active agent % | |
|---|---|---|---|---|---|
| Comparison agent | 20 | 50 | 10 Prop. M. | 20 | Fatty alcohol polyglycol ether sulfate Na |
| 1 | 18 | 52 | 10 Prop. M. | 20 | Lauryldimethylamine oxide |
| 2 | 19 | 53 | 10 Prop. M. | 18 | $C_{12}-C_{18}$-alkyldimethylamine oxide |
| 3 | 19 | 60 | without | 21 | Fatty acid amidopropyldimethylamine oxide |
| 4 | 19 | 57 | without | 24 | Coconut alkyldimethylaminoacetic acid (betaine) |
| 5 | 19 | 56 | without | 25 | Coconut alkylaminopropionic acid |
| 6 | 19 | 51 | 10 Prop. M. | 20 | N-lauryl-β-iminodipropionic acid |

TABLE 1-continued

A) Composition and stability of active substance formulations according to the invention

| | | | | | |
|---|---|---|---|---|---|
| 7 | 19 | 62,5 | without | 19.5 | $C_7$-$C_{17}$-alkoylamino-3-dimethylaminopropane-3-carboxymethylbetaine |
| 8 | 19 | 51 | 10 Prop. M. | 20 | Betaine of the monosodium salt of an acetic acid-substituted and ethoxyacetic acid-substituted coconut alkylimidazoline |
| 9 | 18 | 60 | without | 22 | Alkylhydroxyethylhydroxypropylimidazolesulfonic acid |
| 10 | 19 | 51 | 10 Prop. M. | 20 | Coconut fatty acid amidopropylhydroxysulfobetaine |
| 11 | 18 | 62,5 | without | 19.5 | Betaine of a polysiloxanedimethylaminoacetic acid |

| Formulation No. | Form of appearance after 14 days at 20° C. | 0° C. | below 0° C. from | Chem. stability after 3 months 50° C. |
|---|---|---|---|---|
| Comparison agent | clear | clear | −3° C. cloudy | stable |
| 1 | clear | clear | −3° C. cloudy | stable |
| 2 | clear | clear | −18° C. cloudy | stable |
| 3 | clear | clear | −7° C. cloudy | stable |
| 4 | clear | clear | −13° C. cloudy | stable |
| 5 | clear | clear | −18° C. cloudy | stable |
| 6 | clear | clear | −6° C. cloudy | stable |
| 7 | clear | | +2° C. crystals | — |
| 8 | clear | clear | −1° C. cloudy | stable |
| 9 | clear | +4° C. cloudy | −8° C. solid | — |
| 10 | clear | clear | −10° C. cloudy | stable |
| 11 | clear | clear | up to −25° C. clear | stable |

| Formulation No. | Active substance % | Water % | Organic Solvent % | Surface-active agent % | |
|---|---|---|---|---|---|
| 12 | 20 | 60 | without | 20 | $C_{12}$–$C_{16}$-alkylsulfate, Na |
| 13 | 20 | 37.5 | 20 M. glyc. | 10 | $C_{12}$–$C_{16}$-alkylsulfate, Na |
| | | | | 12,5 | $C_{12}$–$C_{18}$-alkanesulfonate, Na |
| 14 | 20 | 60 | without | 20 | Isodecylsulfosuccinic acid monoester, Na |
| 15 | 20 | 50 | 10 Prop. M | 20 | Isodecylsulfosuccinic acid monoester, Na |
| 16 | 18 | 60 | without | 14 | Isodecylsulfosuccinic acid monoester, Na |
| | | | | 8 | Fatty alcohol polyglycol ether sulfate, Na |
| 17 | 11 | 54 | without | 21 | Isodecylsulfosuccinic acid monoester, Na |
| | | | | 14 | Fatty alcohol polyglycol ether sulfate, Na |
| 18 | 20 | 40 | 20 M. glyc. | 20 | Diisooctylsulfosuccinic acid ester, Na |
| 19 | 20 | 40 | 20 N. glyc. | 12 | Diisooctylsulfosuccinic acid ester, Na |
| | | | | 8 | Fatty alcohol polyglycol ether sulfate, Na |
| 20 | 19 | 41 | 10 Prop. M | 20 | α-olefinesulfonate, Na |
| 21 | 19 | 41 | 10 Prop. M | 5 | α-olefinesulfonate, Na |
| | | | | 15 | Fatty alcohol polyglycol ether sulfate, Na |
| 22 | 19 | 41 | 20 M. glyc. | 10 | α-olefinesulfonate, Na |
| 23 | 19 | 42 | 20 M. glyc. | 11.5 | $C_{12}$–$C_{18}$-alkanesulfonate, Na |
| | | | | 7.5 | Fatty alcohol polyglycol ether sulfosuccinic acid monoester, Na |
| | | | | 12 | $C_{12}$–$C_{18}$-alkanesulfonate Na |
| 24 | 19 | 51 | 10 PEG 200 | 8 | Fatty alcohol polyglycol ether sulfosuccinic acid monoester, Na |
| 25 | 19 | 41 | 20 M. glyc. | 8 | Fatty alcohol polyglycol ether sulfosuccinic acid monoester, Na |
| | | | | 12 | Fatty alcohol polyglycol ether sulfate, Na |
| 26 | 19 | 51 | without | 18 | Decylalcohol polyglycol ether sulfosuccinic acid ester, Na |
| 27 | 19 | 41 | 20 M. glycl. | 5 | Decylalcohol polyglycol ether sulfosuccinic acid ester |
| | | | | 15 | Fatty alcohol polyglycol ether sulfate, Na |

| Formulation No. | Form of appearance after 14 days at 20° C. | 0° C. | below 0° C. from | Chem. stability after 3 months 50° C. |
|---|---|---|---|---|
| 12 | Phase separation | | | — |
| 13 | clear | clear | −10° C. cloudy | stable |
| 14 | clear | clear | — | — |
| 15 | clear | clear | −2° C. cloudy | stable |

TABLE 1-continued

A) Composition and stability of active substance formulations according to the invention

| Formulation No. | 20° C. | 0° C. | below 0° C. from | Chem. stability after 3 months 50° C. |
|---|---|---|---|---|
| 16 | clear | clear | −16° C. cloudy | stable |
| 17 | clear | clear | −12° C. cloudy | stable |
| 18 | Phase separation | | | — |
| 19 | Phase separation | | | — |
| 20 | clear | clear | −5° C. solid | stable |
| 21 | clear | clear | −5° C. solid | |
| 22 | clear | clear | −2° C. cloudy | stable |
| 23 | clear | clear | −18° C. cloudy | stable |
| 24 | clear | clear | −2° C. cloudy | stable |
| 25 | clear | clear | −3° C. cloudy | stable |
| 26 | clear | clear | −11° C. cloudy | stable |
| 27 | clear | clear | −10° C. solid | stable |

| Formulation No. | Active substance % | Water % | Organic Solvent % | Surface-active agent % | |
|---|---|---|---|---|---|
| 28 | 20 | 60 | without | 12 | Dodecylbenzenesulfonate, Na |
|    |    |    |         | 8  | Fatty alcohol polyglycol ether sulfate, Na |
| 29 | 20 | 42 | 20 M. glyc. | 18 | $C_{12}$–$C_{18}$-alkanesulfonate, Na |
| 30 | 20 | 50 | 10 Prop. M. | 12 | $C_{12}$–$C_{18}$-alkanesulfonate, Na |
|    |    |    |             | 8  | Fatty alcohol polyglycol ether sulfate, Na |
| 31 | 20 | 50 | 10 Prop. M  | 6  | $C_{12}$–$C_{18}$-alkanesulfonate, Na |
|    |    |    |             | 14 | Fatty alcohol polyglycol ether sulfate, Na |
| 32 | 11 | 39 | 10 Prop. M  | 20 | $C_{12}$–$C_{18}$-alkanesulfonate, Na |
|    |    |    |             | 20 | Fatty alcohol polyglycol ether sulfate, Na |
| 33 | 14 | 36 | 10 Prop. M. | 40 | Fatty alcohol polyglycol ether sulfate, Na |
| 34 | 10 L | 69 | without | 21 | Coconut alkyldimethylaminoacetic acid |
| 35 | 6.6 L | 60.4 | without | 33 | Coconut alkyldimethylaminoacetic acid |
| 36 | 6.6 L | 67.9 | without | | Decylalcohol polyglycol ether sulfosuccinic acid ester, Na |
| 37 | 9.9 L | 68.2 | without | 14.3 | Isodecylsulfosuccinic acid monoester, Na |
|    |       |      |         | 7.6  | Fatty alcohol polyglycol ether sulfate, Na |
| 38 | 6.6 L | 80.4 | without | 13 | $C_{12}$–$C_{18}$-alkanesulfonate, Na |
| 39 | 6.6 L | 70.4 | 10 PEG 200 | 3 | $C_{12}$–$C_{18}$-alkanesulfonate, Na |
|    |       |      |            | 10 | Fatty alcohol polyglycol ether sulfate, Na |
| 40 | 6.4 L | 70.6 | 10 Prop. M. | 13 | Fatty alcohol polyglycol ether sulfate, Na |
| 41 | 6.4 L | 43.6 | 10 Prop. M. | 40 | Fatty alcohol polyglycol ether sulfate, Na |
| 42 | 10.3 L | 59.7 | 10 Prop. M. | 20 | Fatty alcohol polyglycol ether sulfate, Na |
| 43 | 10.0 L | 40 | 10 Prop. M. | 40 | Fatty alcohol polyglycol ether sulfate, Na |

| Formulation No. | Form of appearance after 14 days at | | | Chem. stability after 3 months 50° C. |
|---|---|---|---|---|
| | 20° C. | 0° C. | below 0° C. from | |
| 28 | Phase separation | | −1° C. solid | — |
| 29 | clear | clear | −16° C. cloudy | stable |
| 30 | clear | clear | −10° C. cloudy | stable |
| 31 | clear | clear | −10° C. cloudy | stable |
| 32 | clear | clear | −10° C. cloudy | stable |
| 33 | clear | ° C. cloudy | | stable |
| 34 | clear | clear | −15° C. cloudy | stable |
| 35 | clear | clear | −7° C. cloudy | stable |
| 36 | clear | clear | −8° C. cloudy | stable |
| 37 | clear | clear | −13° C. cloudy | stable |
| 38 | | cloudy at RT | | |
| 39 | clear | clear | −8° C. cloudy | stable |
| 40 | clear | clear | −3° C. cloudy | stable |
| 41 | clear | clear | −1° C. cloudy | stable |
| 42 | clear | clear | −2° C. cloudy | stable |
| 43 | clear | clear | −10° C. cloudy | stable |

Na = sodium salt or disodium salts in the case of sulfosuccinic acid monoesters
M. glyc. = ethyleneglycol monomethyl ether
clear = clear solution
Active substance: phosphinothricin (ammonium salt)
L: L isomer
Prop. M = propyleneglycol monomethyl ether
PEG 200 = polyethyleneglycol having a mean molecular weight of 200
cloudy = liquid, cloudiness caused by crystals B) Biological examples

EXAMPLE 1

Barley plants which have been grown in the greenhouse were sprayed in the 3-leaf stage with formulations diluted in water (active substance: phosphinothricin ammonium salt) with the active substance concentrations indicated in Table 2. The comparison agent mentioned in Table 1 acted as the control. The plants were scored after 17 days. The damage (action) is expressed as a percentage. The results are represented in Table 2.

TABLE 2

Greenhouse experiment on barley
Action as a percentage 17 days after treatment
Water application rate: 300 l/ha

| Formulation from Table 1 | Dosage: g of active substance/ha | | | | |
|---|---|---|---|---|---|
| No. | 31.25 | 62.5 | 125 | 250 | 500 |
| comparison agent | — | 7 | 67 | 87 | 88 |
| 1 | — | 25 | 80 | 96 | 100 |
| 2 | — | 25 | 78 | 94 | 99 |
| 3 | — | 20 | 75 | 93 | 98 |
| 4 | — | 25 | 75 | 95 | 99 |
| 5 | — | 20 | 78 | 96 | 100 |
| 34 | 22 | 75 | 94 | 99 | |
| 35 | 30 | 82 | 95 | 100 | |

EXAMPLE 2

In a field experiment, oilseed rape, field bean and white goosefoot were sprayed in the 3–5 leaf stage with the formulations according to the invention which had been diluted in water. The water application rate was 300 l/ha. The plants were scored 13 days after the treatment. The damage is expressed as a percentage. The active substance concentration and the experimental results are represented in Table 3.

TABLE 3

Field experiments on oilseed rape, field bean and white goosefoot
Action as a percentage 13 days after treatment

| Formulation from Table 1 | Dosage in kg of active substance/ha | | | | | |
|---|---|---|---|---|---|---|
| | Oilseed rape | | Field bean | | White goosefoot | |
| No. | 0.5 | 1.0 | 0.5 | 1.0 | 0.5 | 1.0 |
| Comparison agent | 73 | 85 | 91 | 99 | 88 | 96 |
| 23 | 75 | 90 | 96 | 100 | 93 | 99 |
| 24 | 80 | 90 | 95 | 99 | 92 | 93 |
| 25 | 82 | 90 | 95 | 100 | 94 | 97 |
| 26 | 78 | 94 | 95 | 99 | 93 | 95 |
| 27 | 80 | 95 | 96 | 99 | 92 | 95 |
| 29 | 82 | 92 | 95 | 98 | 90 | 96 |
| 30 | 81 | 92 | 96 | 99 | 92 | 96 |
| 31 | 80 | 94 | 99 | 100 | 92 | 96 |
| 32 | 92 | 96 | 98 | 100 | 96 | 96 |

EXAMPLE 3

In order to determine the rain resistance of the formulations according to the invention, barley plants which had been grown in the greenhouse were sprayed in the 3-leaf stage with solutions of the various formulations (water application rate 300 l/ha). Some of the plants were exposed to artificial overhead irrigation about 3 hours after this treatment, approximately 10 mm of artificial rain being applied. The activity (damage to the plant) was scored 19 days after this treatment. The active compound concentrations and the experimental results are represented in Table 4.

TABLE 4

Greenhouse experiments on barley without and with overhead irrigation
Dosage in g of active substance/ha
Action as a percentage 19 days after treatment
Overhead irrigation 3 hours after treatment (approx. 10 mm)

| Formulation from Table 1 | Without rain | | | | | With overhead irrigation | | | | |
|---|---|---|---|---|---|---|---|---|---|---|
| No. | 62.5 | 125 | 250 | 500 | 1000 | 62.5 | 125 | 250 | 500 | 1000 |
| Comparison agent | — | 30 | 45 | 75 | 95 | — | 10 | 30 | 65 | 85 |
| 16 | — | 33 | 63 | 85 | 98 | — | 35 | 50 | 75 | 95 |
| 17 | — | 40 | 70 | 88 | 99 | — | 30 | 55 | 85 | 95 |
| 32 | — | 42 | 67 | 93 | 100 | — | 35 | 42 | 75 | 94 |
| 33 | — | 58 | 85 | 95 | 100 | — | 58 | 62 | 80 | 98 |
| 37 (Active substance: L isomer) | 38 | 50 | 80 | 96 | — | 20 | 48 | 75 | 92 | — |
| 38 (Active substance: L isomer) | 35 | 50 | 82 | 96 | — | 25 | 45 | 75 | 95 | — |
| 40 (Active substance: L isomer) | 30 | 50 | 78 | 94 | — | 15 | 25 | 70 | 85 | — |
| 41 (Active substance: L isomer) | 45 | 65 | 90 | 98 | — | 33 | 55 | 80 | 93 | — |
| 42 (Active substance: L isomer) | 35 | 45 | 72 | 96 | — | 10 | 35 | 60 | 82 | — |
| 43 (Active substance: L isomer) | 55 | 85 | 95 | 99 | — | 40 | 60 | 80 | 99 | — |

EXAMPLE 4

In order to test the formulations according to the invention for rain resistance, an experiment with Paspalum conjugatum, a perennial Graminea, was set up in an olivetree plantation. After the plants had been sprayed with solutions of the various formulations, some of the plants were exposed to artificial overhead irrigation, an artificial rain of an amount of precipitation of approx. 20 mm being applied. The activity (damage to the plants) was scored 2 weeks after this treatment. The active substance concentrations and experimental results are represented in Table 5.

TABLE 5

Field experiment on Paspalum conjugatum
Action as a percentage 2 weeks after treatment
Overhead irrigation 4 hours after 20 mm's treatment

| Formulation from Table 1 No. | | Without overhead irrigation | | With overhead irrigation | |
|---|---|---|---|---|---|
| | g of a i /ha | 400 | 500 | 400 | 500 |
| Comparison agent | | 85 | 95 | 20 | 30 |
| 33 | | 90 | 98 | 75 | 82 |
| | g of a i /ha | 200 | 250 | 200 | 250 |
| 41 | | 95 | 99 | 80 | 85 |

We claim:
1. A liquid herbicidal agent consisting of a compound of the formula

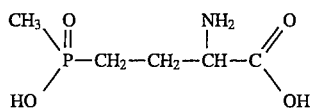

in the form of the racemate or of the L enantiomer, lower alkyl esters thereof or salts thereof with acids or bases (I) in combination with surfactants in the form of (a) ($C_{12}$–$C_{18}$)-alkyldimethyl-, ($C_{10}$–$C_{18}$)-fatty acid amidopropyldimethyl- or ($C_{10}$–$C_{18}$)-fatty acid amidoethyldimethylamine oxides or (b) the betaine of coconut alkyldimethylaminoacetic acid or of coconut alkylaminopropionic acid or (c) mixtures of ($C_{12}$–$C_{18}$)-alkanesulfonates with ($C_{10}$–$C_{18}$)-fatty alcohol polyglycol ether sulfosuccinic acid monoesters or (d) ($C_{12}$–$C_{18}$)-alkylsulfosuccinic acid monoesters or ($C_{10}$–$C_{18}$)-fatty alcohol polyglycol ether sulfosuccinic acid monoesters and ($C_{10}$–$C_{18}$)-fatty alcohol polyglycol ether sulfosuccinic acid esters and their mixtures with ($C_{10}$–$C_{18}$)-fatty alcohol polyglycol ether sulfates or (e) ($C_{12}$–$C_{18}$)-α-olefinsulfonates and mixtures thereof with ($C_{10}$–$C_{18}$)-fatty alcohol polyglycol ether sulfates, ($C_{10}$–$C_{18}$)-fatty alcohol polyglycol ether sulfosuccinic acid monoesters or ($C_{12}$–$C_{18}$)-alkylsulfosuccinic acid monoesters, sulfonates which can be used being alkali metal salts, ammonium salts, alkaline earth metal salts or substituted alkyl- or alkanolamine salts of the corresponding sulfonic or sulfuric acids.

2. A herbicidal agent as claimed in claim 1, which contains a surfactant selected from the group consisting of ($C_{12}$–$C_{18}$)-alkyldimethylamine oxides, ($C_{12}$–$C_{18}$)-alkylsulfosuccinic acid monoesters, ($C_{12}$–$C_{20}$)-α-olefinsulfonates or mixtures of ($C_{12}$–$C_{20}$)-α-olefin-sulfonates with ($C_{10}$–$C_{18}$)-fatty alcohol polyglycol ether sulfates.

3. A herbicidal agent as claimed in claim 1, which contains, as surfactants, isodecylsulfosuccinic acid monoester or its mixtures with ($C_{10}$–$C_{18}$)-fatty alcohol polyglycol ether sulfates.

4. A herbicidal agent as claimed in claim 1, which contains, besides 5–40% by weight of a compound I, the 0.5-8-fold proportion by weight of the surfactants according to the invention.

5. Method of controlling undesired plants, wherein an active amount of the herbicidal agent as claimed in claim 1 is applied to these plants or the agricultural areas.

* * * * *